United States Patent [19]

Ito et al.

[11] Patent Number: 5,079,154

[45] Date of Patent: Jan. 7, 1992

[54] MUTANT RESISTANT TO CELL MEMBRANE SYNTHESIS INHIBITOR AND PROCESS FOR PREPARING THE SAME

[75] Inventors: Susumu Ito, Utsunomiya; Masaharu Shimooka, Tochigi; Yuichi Ohta, Ibaraki; Mikio Takaiwa, Tochigi; Shigehito Adachi, Utsunomiya, all of Japan

[73] Assignee: Kao Corporation, Tokyo, Japan

[21] Appl. No.: 252,049

[22] Filed: Sep. 30, 1988

[30] Foreign Application Priority Data

Mar. 30, 1988 [JP] Japan .................................. 63-77846

[51] Int. Cl.$^5$ ............................................. C12N 15/00
[52] U.S. Cl. ................................. 435/172.1; 435/252.5
[58] Field of Search ................ 435/252.1, 832, 252.31, 435/172.1, 252.5

[56] References Cited

FOREIGN PATENT DOCUMENTS 50-28515  9/1975  Japan .
0224686  12/1983  Japan .
0019483  1/1986  Japan .

OTHER PUBLICATIONS

*Bergey's Manual of Systematic Bacteriology, vol. 2*, Sneath et al. (ed.), Williams & Wilkins, Baltimore, 1986, pp. 1104–1129.

J. Gen. Appl. Microbiol., vol. 31, No. 4, 1985, pp. 323-328; B. Maruo et al.: "Stepwise enhancement of productivity of thermostable amylase in *Bacillus licheniformis* by a series of mutation".

Agric. Biol. Chem., vol. 43, No. 11, 1979, pp. 2343-2349; K. Hitotsuyanagi et al.: "Stepwise introduction of regulatory genes stimulating production of alpha-amylase into *Bacillus substillis*: construction of an alpha-amylase extrahyper producing strain".

Biochemical and Biophysical Research Communications, vol. 70, No. 1, 1976, pp. 125–131, Academic Press, Inc., T. Sasaki et al.: "Hyperproductivity of extracellular alpha-amylase by a tunicamycin resistant mutant of *Bacillus subtilis*".

Chemical Abstract, vol. 93, No. 7, Aug. 1980, p. 735, Abstract No. 68681y, Columbus, Ohio, US; & JP-A-80 48 387 (B. Maruo et al.) 07-04-1980.

Chemical Abstracts, vol. 93, No. 7, Aug. 1980, p. 735, Abstract No. 686846 Columbus, Ohio, US; & JP-A-80 34 047 (B. Maruo) 10-03-1980.

Chemical Abstracts, vol. 97, No. 7, Aug. 1982, p. 496, Abstract No. 54008e Columbus, Ohio, US; & JP-A-82 47 479 (J. Utaka) 18-03-1982.

*Purification and Properties of a Cellulase from Alkalophilic Bacillus sp. No. 1139* by Fumiyasu Fukumori, et al. Journal of General Microbiology (1985), 131, 3339-3345.

*Primary Examiner*—James Martinell
*Attorney, Agent, or Firm*—Oblon, Spivak, McClelland, Maier & Neustadt

[57] ABSTRACT

A mutant of an extracellular enzyme-producing microorganism belonging to genus Bacillus, which is resistant to a cell membrane synthesis inhibitor, including vancomycin and ristocetin, is disclosed. The cell membrane synthesis inhibitor-resistant mutant can produce such an enzyme as cellulase, protease, or amylase about 2 to 4 times of the parent strain. Such a mutant can be produced by subjecting an extracellular enzyme-producing microorganism tot a mutation treatment, and culturing said microorganism in a culture medium containing a cell membrane synthesis inhibitor.

3 Claims, No Drawings

MUTANT RESISTANT TO CELL MEMBRANE SYNTHESIS INHIBITOR AND PROCESS FOR PREPARING THE SAME

BACKGROUND OF THE INVENTION

1. Field of the Invention

This invention relates to a mutant which is resistant to a cell membrane synthesis inhibitor, and, more particularly, to a cell membrane synthesis inhibitor-resistant mutant of an extracellular enzyme-producing microorganism belonging to genus Bacillus, such as cellulase-, protease-, or amylase-producing microorganism belonging to genus Bacillus. The invention also relates to a process for preparing such a mutant.

2. Description of the Background

Cellulase is realized as a group of complicated enzymes catalyzing enzymatic reactions decomposing cellulose into glucose, cellobiose, or even into a cello-oligosaccharide. Depending on the functions, it encompasses enzymes such as $C_x$ cellulase (CMC-ase or endo-$\beta$-1,4-glucanase), $C_1$ cellulase (cellobiohydrolase or exo-$\beta$-1,4-glucanase), and $\beta$-glucosidase (cellobiose $\beta$-1,4-glucosidase), and the like.

Conventionally, studies on cellulase have been directed, for the most part, to the effective utilization of biomass resources. For this reason major supply sources of cellulase have been fungus belonging to genera such as Trichoderma, Aspergillus, Acremonium, Humichola, and the like.

Recent development of a new application of cellulase as an additive to detergents for washing clothes is requiring supply of alkaline cellulase having a better stability and exhibiting maximum activity at a pH of alkaline side at which cloth washing is performed with a better efficiency.

There have been known several processes for producing alkaline cellulase. Until recently, such processes have been typified by a process for collecting cellulase A from a culture broth of an alkalophilic microorganism belonging to genus Bacillus (Japanese Patent Laid-open No. 28515/1985), a process for producing alkaline cellulase 301-A through culturing of a microorganism belonging to genus of Cellulomonas (Japanese Patent Laid-open No. 224686/1983), a process for obtaining carboxymethyl cellulase through culturing of an alkalophilic strain, Bacillus sp. no. 1139 [Fukumori F., Kudo T., and Horikoshi K.; *J. Gen. Microbiol.*, 131, 3339 (1985)], a process for producing alkaline cellulase with the use of a microorganism belonging to Streptomyces (Japanese Patent Laid-open No. 19483/1986). Micrcorganism used in these processes had only a low alkaline cellulase productivity and thus the processes have not been suitable for industrial application.

In view of this situation the present inventors have undertaken extensive studies in order to obtain a micrcorganism having a better alkaline cellulase productivity. As a result, inventors have previously discovered several novel microorganisms having superior alkaline cellulase producing capability, including Bacillus sp. KSM-635 (FERM 8872), and filed patent applications on these microorganisms (Japanese Patent Application No. 257775/1986 and others).

Formulating protease into detergents have long been practiced. Earlier practice was to formulate into detergents protease having an optimum pH close to the neutral region such as papain, pancreas trypsin, or the like. Like cellulase, however, protease having an optimum pH in an alkaline side and stable in surface active agents have been desired for the detergent use. Development of such protease has been undertaken.

Typical alkaline proteases used for detergent purpose are alkalase, savinase, esperase (manufactured by Novo Industries Co.), maxatase (produced by Gist Brocades Co.), and the like. The optimum reaction temperature for these enzymes is in the neighborhood of 60° C. and is in conformity with the washing practice of some region, for example, European countries and U.S.A.

However, in other regions where washing is performed near room temperature, supply of protease are desired which has a strong activity at a temperature lower than that at which conventional protease are active. Furthermore, because of common knowledge that a protease with a superior capability of decomposing insoluble proteins such as keratin can contribute to detergency [Minagawa M.; Sensho-shi (*J. Jpn. Res. Assn. Text. End-Uses*, 26, 322 (1985)], the desire has existed for a protease having a superior insoluble protein decomposing capability.

The present inventors have carried out extensive studies in order to obtain an alkaline protease having keratin-decomposing capability, and a lower optimum temperature, i.e., exhibiting high activity at a low temperature, and discovered a group of microorganisms, including Bacillus sp. KSM-2001 (FERM P-9449), satisfying these requirements. The inventors previously filed a patent application (Japanese Patent Application No. 261487/1987) based on these findings.

Attention has been given also to amylase capable of hydrolyzing starch as a component of detergents, since starch are abunduntly contained in the dirt of foods and the like. Examples of known amylases are neutral amylase produced, for example, by *Bacillus amyloliquefaciens* [N. E. Welker and L. L. Campbell; *J. Bacteriol.*, 94, 1124, (1967)], heat resistant amylase produced, for example, by *Bacillus licheniformis* (Japanese Patent Laid-open No. 37094/1986), alkaline amylase produced, for example, by *Bacillus ohbensis* (Japanese Patent Publication No. 31949/1977), and the like.

Development of the above-mentioned new microorganisms has made it possible to produce extracellular enzymes for practical application. For the purpose of industrial production, however, a need has continued to exist for the further development of extracellular enzyme-producing microorganisms other than those mentioned above, as well as improvement in productivity of extracellular enzyme by microorganisms.

In this situation the inventors have undertaken continued studies for the improvement of productivity of extracellular enzymes, especially by means of mutation, and found that a remarkable productivity improvement was attained by providing extracellular enzyme-producing microorganisms belonging to genus Bacillus with resistance to antibiotics cell membrane synthesis inhibitors. This finding has led to the completion of this invention.

SUMMARY OF THE INVENTION

Accordingly, an object of this invention is to provide a cell membrane synthesis inhibitor-resistant mutant of an extracellular enzyme-producing microorganism belonging to genus Bacillus.

Another object of this invention is to provide a process for producing a cell membrane synthesis inhibitor-resistant mutant of an extracellular enzyme-producing microorganism belonging to genus Bacillus, comprising:

subjecting an extracellular enzyme-producing microorganism to a mutation treatment, and culturing said microorganism in a culture medium containing a cell membrane synthesis inhibitor.

Other objects, features and advantages of the invention will hereinafter become more readily apparent from the following description.

DETAILED DESCRIPTION OF THE INVENTION AND PREFERRED EMBODIMENTS

A cell membrane synthesis inhibitor used in this invention is defined as a substance inhibiting the lipid cycle involved in the cell membrane synthesis in a microorganism. Following antibiotics are given as examples of such substances:

Vancomycin, Ristocetin: These substances inhibit the polymerization reaction of undecaprenol-PP-MurNAc(-GlcNAc)-peptide, a lipid intermediate, to produce a linear glycopeptide [Anderson, J. S. et al, *Proc. Natl. Acad. Sci. U.S.A.*, 53, 881 (1965); Lugtenberg, E. J. J. et al, *J. Bacteriol.*, 108, 20 (1971)].

Enramycin: [Matsuhashi et al, *Agric. Biol. Chem.*, 33, 134 (1969)]

Macarbomycin [Suzuki et al, *J. Antibiot.*, 25, 94 (1972)]

Moenomycin, Prasinomycin, Diumycin [Tanaka, N., "Mechanism of Antibiotic Action" Tokyo University Press, Tokyo, Japan, 1978]

The cell membrane synthesis inhibitor-resistant mutant of an enzyme-producing microorganism belonging to genus of Bacillus of this invention (such mutant being hereinafter referred to as "inhibitor-resistant mutant") can be produced by inducing mutation in an extracellular enzyme-producing microorganism belonging to genus Bacillus (hereinafter referred to as "parent strain") through conventional method such as reaction of a mutagenic agent on the parent strain or irradiation of UV rays or radioactive rays, culturing the mutant thus produced in a culture medium containing a cell membrane synthesis inhibitor, such as vancomycin or ristocetin, at a high concentration, and collecting cells which are resistant to the cell membrane synthesis inhibitor.

Any microorganisms belonging to genus Bacillus and possessing extracellular enzyme-producing capability can be used as a parent strain. Preferable parent strains are cellulase-, protease-, or amylase-producing microorganisms, and specifically include, as cellulase-producing parent strains, Bacillus sp. KSM-635 (Japanese Patent Application No. 257775/1986), Bacillus sp. KSM-425 (FERM-P 9007) (Japanese Patent Application No. 283742/1986), Bacillus sp. KSM-521 (FERM-P 9009) (Japanese Patent Application No. 57644/1987), and Bacillus sp. KSM-580 (FERM-P 9013) (Japanese Patent Application No. 68597/1987), all previously discovered by the present inventors in the soils in Hagagun, Tochigi-ken, Japan; as protease-producing parent strains, Bacillus sp. KSM-2001, (FERM-P 9449) Bacillus sp. KSM-2002, Bacillus sp. KSM-2003, (FERM-P 9451) and Bacillus sp. KSM-2005, (FERM-P 9453) all of which were discovered by the present inventors in the soils in Haga-gun, Tochigi-ken, Japan and filed for patent (Japanese Patent Application No. 261487/1987); and as amylase-producing microorganisms, *Bacillus amyloliquefaciens* KSM-21 (ATCC 23844), *Bacillus amyloliquefaciens* KSM-22 (ATCC 23845), and *Bacillus licheniformis* KSM-23 (ATCC 27811).

Given as examples of chemicals inducing mutation are bases or base-like substances, including 5-bromouracil, bromodeoxyuridine, and the like, acridine, nitrous acid, hydroxylamines, alkylating reagents such as ethylmathane sulfonate (EMS), N-methyl-N'-nitrosoguanidine (NTG), mustard gas, and the like. Ionizing radiation and ultraviolet radiation ar given as examples of radiation.

The term "inhibitor-resistant" as used in this invention means the state of a microorganism capable of growing in the conditions where a cell membrane synthesis inhibitor is present at a concentration of at least the minimum inhibitory concentration (MIC) of the parent strain. Therefore, in order to select inhibitor-resistant strains among from mutants, MIC of the parent strain is first measured, a mutant is cultured in a medium containing the cell membrane synthesis inhibitor of a concentration above the MIC, and cells forming colony is collected.

Typical examples of inhibitor-resistant strains of cellulase-producing microorganisms are vancomycin-resistant Bacillus sp. KSM-635$_v$ and ristocetin-resistant Bacillus sp. KSM-635$_r$, both having been induced from Bacillus sp. KSM-635 as the parent strain. Mycological characteristics of these two antibiotic-resistant strains are now discussed.

(1) Observation under microscope

Cells are gram-positive rods of a size of 0.5–1.2 $\mu m \times 1.5$–4.0 $\mu m$, with an endospore (0.7–1.2 $\mu m \times 1.0$–2.0 $\mu m$) forming at one of their ends. They have flagella and are motile.

(2) Growth in various culture media

Cells grow in a pH range of 8 to 11. Growth is most proliferous in a medium to which 0.5 to 1.0% of sodium carbonate ($Na_2CO_3$) is added. The mycological characteristics of the cells described bellow are those in the presence of 1.0% by weight of $Na_2CO_3$.

(a) Nutrient agar plate

Colony has a circular shape, with it surface being flat. The color of the colony is white - yellow, semi-transparent, and glossy.

(b) Nutrient broth Cells can grow and the broth become turbid. Cells do not grow in a neutral pH.

(c) Cells can grow in nutrient broth containing 7% NaCl.

(d) Nutrient agar containing gelatin Cells do not grow.

(e) Litmus milk medium Milk is not coagulated. Peptonization: negative

Physiological characteristics (a) Nitric acid reduced to nitrite: positive Denitrification: negative (b) MR test: undeterminable VP test: positive (c) Do not produce indole (d) Production of hydrogen sulfide: negative (e) Do not hydrolyze or utilize starch (f) Utilize citric acid (g) Utilize nitric acid and nitrous acid. Utilize ammonium chloride only slightly, but utilize ammonium phosphate efficiently.

(h) Turn light yellow, but are not fluorescent on King B agar plate (i) Urease: negative (j) Oxidase: unclear (k) Catalase: positive (l) Growth temperature: 20°–45° C., Optimum growth temperature: 29°–37° C.
(m) Growth pH range: 8–11
   Optimum pH range: 9.5–10.2
(n) Behavior on oxygen: aerobic
(o) Sugar utilization
Utilize D-ribose, L-arabinose, D-xylose, D-glucose, D-mannose, D-fructose, maltose, sucrose, trehalose, D-mannitol, inositol, and glycerol, and do not utilize D-galactose, lactose, D-sorbitol, starch, dextrin, and raffinose.
(p) Hydrolysis of casein and gelatin: negative
(q) Require biotin (or desthiobiotin) for the growth The above-mentioned characteristics of inhibitor-resistant mutant strains, Bacillus sp. KSM-635$_v$ and Bacillus sp. KSM-635$_r$, are the same as those of the parent strain, Bacillus sp. KSM-635. However, different from the parent strain these two inhibitor-resistant mutants can grow in the presence of vancomycin or ristocetin, and possess alkaline cellulase-producing capability 2 to 4 times greater than the parent strain.

Based on the above-mentioned similarity of the inhibitor-resistant mutants to the parent strain, the mutants are judged as belonging to the same group as the parent strain, an alkalophilic Bacillus, which was defined by Horikoshi and Akiba as the Bacillus "growing in an alkaline medium of the pH of at least 8 but not below pH 8 [*Alkalophilic Microorganisms*, Japan Scientific Society Press (Tokyo), 1982].

Typical examples of inhibitor-resistant strains of protease-producing microorganisms are vancomycin-resistant Bacillus sp. KSM-2002$_v$ and ristocetin-resistant Bacillus sp. KSM-2002$_r$, both having been induced from Bacillus sp. KSM-2002 as the parent strain. Mycological characteristics of these two inhibitor-resistant strains are as follows:

(1) Observation under microscope
Cells are gram-positive rods of a size of 0.5–0.8 μm×1.5–3.0 μm, with a circular or oval endospore (0.4–0.8 μm×0.4–0.8 μm) forming at central-subterminal of the cell. They have peripheral flagella and are motile.

(2) Growth in various culture media
(a-i) Nutrient agar plate
Cells form circular, convex, or smooth wave-like colonies with a diameter of 1.0 to 5.0 mm. The colony has a dewdrop shape with a smooth, fatty, semi-transparent surface colored pale yellow - milky white.
(a-ii) Nutrient agar slant
Grow only weakly forming a band in a broth at pH 7.0. Colony is milky white and semi-transparent. The band-like growth expands at pH 10.0.
(b) Nutrient broth
Cells can slightly grow at pH 7.0 without forming cell membrane.
(c) Cells can grow in the presence of a 10% sodium chloride.
(d) Stab culturing in nutrient agar
Liquefy gelatin at pH 7.0.
(e) Litmus milk medium
Slightly grow. Milk coagulation and litmus discoloration are not observed.

(3) Physiological characteristics
(a) Nitric acid reduced to nitrite: negative
Denitrification reaction: negative
(b) MR test: negative
VP test: negative
(c) Do not produce indole
(d) Production of hydrogen sulfide: negative
(e) Hydrolysis of starch: negative
(f) Utilization of citric acid: negative (in Christensen-Simons medium)
(g) Utilization of nitric acid and ammonium sulfate: negative
(h) Do not produce pigment.
(i) Urease: negative
(j) Oxidase: positive
(k) Catalase: positive
(l) Growth temperature: 10°–37° C., growth is good at 20°–30° C.
(m) Growth pH range: 6.0–11.0
(n) Grow in either aerobic or anaerobic conditions.
(o) Sugar utilization
Utilize L-arabinose, D-xylose, D-glucose, D-fructose, D-galactose, maltose, lactose, D-sorbitol, D-mannitol, and starch, and not utilize D-mannose, sucrose, trehalose, inositol, and glycerol.
(p) Production of acids and gases from sugars
Both inhibitor-resistant strains do not produce acids and gases from following sugars.
L-arabinose, D-xylose, D-glucose, D-mannose, D-fructose, D-galactose, maltose, sucrose, lactose, trehalose, D-sorbitol, D-mannitol, inositol, glycerol, and starch.

The above-mentioned characteristics of inhibitor-resistant mutant strains, Bacillus sp. KSM-2002$_v$ and Bacillus sp. KSM-2002$_r$, are the same as those of the parent strain, Bacillus sp. KSM-2002. However, different from the parent strain these two inhibitor-resistant mutants can grow in the presence of vancomycin or ristocetin at a concentration above MIC, and possess alkaline protease-producing capability 2 to 3 times greater than the parent strain.

Further, given as typical examples of inhibitor-resistant strains of amylase-producing microorganisms are vancomycin-resistant *Bacillus amyloliquefaciens* KSM-22$_v$ and ristocetin-resistant *Bacillus amyloliquefaciens* KSM-22$_r$, both having been induced from a known microorganism, *Bacillus amyloliquefaciens* KSM-22 [ATCC 23845; N. E. Welker and I,. L. Campbell, *J. Bacteriol.*, 94, 1124 (1967)], as the parent strain. These inhibitor-resistant mutant strains have the same mycological characteristics as the parent strain, *Bacillus amyloliquefaciens* KSM-22. However, different from the parent strain the inhibitor-resistant mutants can grow in the presence of vancomycin or ristocetin, and possess amylase-producing capability 1.3 to 4 times greater than the parent strain.

Culturing of the inhibitor-resistant mutant of this invention may be carried out by inoculating the cells into a normal liquid medium and culturing the cells according to a conventional aerobic culture method. Inclusion of a suitable amount of carbon and nitrogen sources which the microorganism can utilize in the medium is desirable. There are no specific limitations as to the carbon and nitrogen sources. Given as examples of carbon sources are fibrous substances such as chaff, hull, filter paper, general paper, sawdust; molasses, invert sugar, CMC, Avicel, cellulose powder, xylan, pectin, soluble starch, and the like. In addition, other utilizable carbon sources are included, such as ribose, arabinose, xylose, glucose, mannose, fructose, galactose, lactose, maltose, sucrose, trehalose, sorbitol, mannitol, inositol, glycerol, as well as organic acid such as citric acid, acetic acid, and the like. Enumerated as nitrogen sources are inorganic nitrogen-containing compounds such as ammonium nitrate, ammonium sulfate, ammonium chloride, ammonium phosphate, sodium nitrate, and the like; corn gluten meal, soybean flour, soybean meal, corn steep liquor, casamino acid, yeast extract, pharma media, sardine meal, meat extract, peptone, hypro, ajipower, corn-soybean meal, coffee meal, cotton seed meal, cultivator, amiflex, ajipron, zest, ajix, and the like. In addition to these carbon and nitrogen sources, phosphoric acid, salts of metal such as $Mg^{+2}$, $Ca^{+2}$, $Mn^{+2}$, $Zn^{+2}$, $Co^{+2}$, $Na^+$, $K^+$, and the like, as required, other micro-nutritious organic or inorganic substances can be added into the culture medium.

Enzymes such as cellulase, protease, amylase produced by the inhibitor-resistant mutant outside the cells can be collected and purified by a conventional method. The culture liquid containing such an enzyme can be used as is as an enzyme source. Such an enzyme liquid may be obtained by separating cells from the culture broth by means of centrifugation, filtration, or the like, and by precipitating proteins by a conventional method, including salting out, isoelectric precipitation, precipitation from solvent, or the like, from the cells or the culture liquid filtrate, or by condensing said filtrate by means of ultrafiltration. Desalting can be performed by a conventional method, including dialysis, gel filtration, or the like. Although it is possible to use the enzyme liquid thus obtained as is, they can be served for use after purifying by means of a suitable combination of hydroxyapatite chromatography, ion-exchange chromatography such as DEAE-Sephadex or DEAE-cellulose, molecular sieving gel chromatography, and the like.

Since the inhibitor-resistant mutants of this invention have extracellular enzyme-producing capability of 2 to 4 times of the parent strains, they can be advantageously used for the industrial production of cellulase, protease, amylase, and the like.

Other features of the invention will become apparent in the course of the following description of the exemplary embodiments which are given for illustration of the invention and are not intended to be limiting thereof.

EXAMPLES

In the examples below enzymatic activities were measured according to the following method.

(1) CMC-ase activity

To the solution comprised of 0.2 ml of 25% CMC, 0.1 ml of 0.5M glycine buffer (pH 9.0), and 0.1 ml of deionized water was added 0.1 ml of enzyme solution diluted to an appropriate concentration, and the mixture was reacted for 20 minutes at 40° C. After the reaction, reducing sugar was quantitatively analyzed by 3,5-dinitrosalicylic acid (DNS) method. Specifically, in order to determine the amount of produced reducing sugar 1 ml of DNS reagent was added to 0.5 ml of reaction liquid, and mixture was caused to color by heating at 100° C. for 5 minutes. After cooling, the colored mixture was diluted with 4.5 ml of deionized water and subjected to colorimetric quantitative analysis at 535 nm.

One (1) unit of enzyme titer is defined as the amount of the enzyme producing reducing sugar corresponding to 1 μmol of glucose per minute. Fermentation productivity is expressed by the enzyme unit per 1 liter of the culture liquid.

(2) Protease activity

Following the method proposed by Anson [Anson, M. L., J. Ger. Physiol., 22, 79 (1938)] bovine serum hemoglobin was denatured by urea, and adjusted to pH 10.5 with sodium hydroxide. Into 0.5 ml of this substrate solution (2.2% as hemoglobin) 0.1 ml [$1.0\times10^{-5}$-$1.0\times10^{-3}$ μA.U (A.U.: Anson Unit)] of an enzyme solution was added, and mixture was reacted at 25° C. for 10 minutes, upon which 1.0 ml of 4.9% trichloroacetic acid was added to terminate the reaction. After termination of the reaction, the reaction mixture was centrifuged at 3,000 rpm for 10 minutes. Proteolysates contained in the supernatant was quantitatively analyzed by Folin-Lowry method [O. H. Lowry et al; J. Biol. Chem., 193, 265 (1951)]. 1 A.U. is defined as the amount of enzyme releasing 1 mmol of tyrosine in 1 minutes under the above reaction conditions.

(3) Amylase activity

To the solution comprised of 0.4 ml of 1.25% soluble starch, 0.025 ml of 1M Tris-HCl buffer (pH 7.0), 0.05 ml of 0.2M calcium chloride, and 0.425 ml of deionized water was added 0.1 ml of an enzyme solution diluted to an appropriate concentration, and the mixture was reacted for 5 minutes at 30° C. After the reaction, reducing sugar was quantitatively analyzed by 3,5-dinitrosalicylic acid (DNS) method. Specifically, in order to determine the amount of produced reducing sugar 1 ml of DNS reagent was added to 1 ml of the reaction liquid, and the mixture was caused to color by heating at 100° C. for 5 minutes. After cooling, the colored mixture was diluted with 4 ml of deionized water and subjected to colorimetric quantitative analysis at 535 nm.

One (1) unit of enzyme titer is defined as the amount of the enzyme producing reducing sugar corresponding to 1 μmol of maltose per minute.

REFERENCE EXAMPLE 1

Bacillus sp. KSM-635 (FERM P-8872) was spread on the medium A described below, each medium containing vancomycin at a concentration shown in Table 1 below, to determine minimum inhibitory concentration (MIC). The media A containing vancomycin to which Bacillus sp. KSM-635 (FERM P-8872) was spread was left for 3 days at 30° C., and the cell growth conditions on the medium surface was observed by naked eyes. The results are shown in Table 1.

TABLE 1

| Concentration of vancomycin | Cell growth on medium surface |
|---|---|
| 0 (Control) | +++ |
| 0.1 γ | ++ |
| 0.2 γ | ± |
| 0.3 γ | — |
| 0.5 γ | — |
| 1.0 γ | — |
| 1.5 γ | — |

| Medium A: | |
|---|---|
| Sucrose | 2% |
| Mixed amino acid solution | 6% |
| $KH_2PO_4$ | 0.1% |
| Tris-HCl buffer | 0.1 M |
| | (Final conc. pH 8) |
| Bacto agar-agar | 2.0% |
| Vancomycin | Concentration in Table 1 |

As evident from the table MIC of vancomycin for Bacillus sp. KSM-635 was about 0.2 γ.

REFERENCE EXAMPLE 2

Bacillus sp. KSM-635 (FERM P-8872) was spread on the medium B described below, each medium containing ristocetin at a prescribed concentration, to determine minimum inhibitory concentration (MIC) of the antibiotic. As a result, the MIC of ristocetin for Bacillus sp. KSM-635 (FERM P-8872) was found to be about 0.1 γ.

| Medium B: | |
|---|---|
| Sucrose | 2% |
| Mixed amino acid solution | 6% |
| KH$_2$PO$_4$ | 0.1% |
| Tris-HCl buffer | 0.1 M (Final conc. pH 8) |
| Bacto agar-agar | 2.0% |
| Ristocetin | Suitable concentration |

EXAMPLE 1

Bacillus sp. KSM-635 (FERM P-8872) was inoculated into the liquid medium C and cultured at 30° C. for 20 hours. EMS was added to the culture broth to a concentration of 0.5 to 3% (normally 1%) and the broth was left for 20 minutes at 30° C. Then, a 3% treated cultured liquid was inoculated into the liquid medium and the culturing was continued at 30° C. overnight.

The culture liquid was was spread on medium A containing not less than 0.2 γ of vancomycin and cultured at 30° C. for 2 days. Colonies grown on the surface of the medium were collected. The above culturing procedure was repeated 5 times to obtain 18 vancomycin-resistant strains.

Each of these vancomycin-resistant strains was inoculated into 100 ml of liquid medium D and cultured at 30° C. for 3 days. The alkaline cellulase activity was determined on each broth. As a result, the production of vancomycin-resistant strains with a high alkaline cellulase activity as shown in Table 2 was confirmed. The strain having the highest titer (No. 3215) was named Bacillus sp. KSM-635$_v$. The strain was deposited with Fermentation Research Institute, Agency of Industrial Science and Technology (FERM P-9084).

| Medium C: | |
|---|---|
| Meat extract | 1% |
| Yeast extract | 0.5% |
| NaCl | 0.5% |
| Glucose | 2.0% |
| KH$_2$PO$_4$ | 1.0% |
| Na$_2$CO$_3$ | 0.75% |
| Medium D: | |
| Sugar | 2% |
| Mixed amino acid solution | 6% |
| Yeast extract | 0.2% |
| Na$_2$CO$_3$ | 0.5% |

TABLE 2

| Mutant No. | Vancomycin Resistance Acquired | Alkaline Cellulase Production (unit/l) |
|---|---|---|
| 3215 | 1.0 γ | 16,300 |
| 3422 | 1.0 γ | 14,200 |
| 3424 | 0.5 γ | 9,500 |
| 3681 | 0.5 γ | 11,230 |
| 3691 | 0.5 γ | 14,100 |
| 3693 | 0.5 γ | 10,990 |
| Bacillus sp. KSM-635 (Parent strain: Control) | 0.2 γ | 4,280 |

TABLE 2-continued

| | Ristocetin Resistance | |
|---|---|---|
| 4021 | 1.5 γ | 20,050 |
| 4033 | 1.5 γ | 15,600 |
| 4091 | 1.0 γ | 18,200 |
| 4180 | 0.5 γ | 16,800 |
| Bacillus sp. KSM-635 (Parent strain: Control) | 0.1 γ | 4,590 |

EXAMPLE 2

Bacillus sp. KSM-635 (FERM P-8872) was inoculated into the liquid medium C and cultured at 30° C. for 20 hours. EMS was added to the culture broth to a concentration of 0.5 to 3% (normally 1%) and the broth was left for 20 minutes at 30° C. Then, a 3% treated cultured liquid was inoculated into the liquid medium and the culturing was continued under shaking at 30° C. overnight.

The culture liquid was was spread on medium B containing not less than 0.1 γ of ristocetin and cultured at 30° C. for 2 days. Colonies grown on the surface of the medium were collected. The above culturing procedure was repeated 5 times to obtain 14 ristocetin-resistant strains.

Each of these ristocetin-resistant strains was inoculated into 100 ml of liquid medium D and cultured at 30° C. for 3 days. The alkaline cellulase titer was determined on each broth. As a result, the production of ristocetin-resistant strains with a high alkaline cellulase titer as shown in Table 3 was confirmed. The strain having the highest titer (No. 4021) was named Bacillus sp. KSM-635$_r$. The strain was deposited with Fermentation Research Institute, Agency of Industrial Science and Technology (FERM P-9085).

EXAMPLE 3

Bacillus sp. KSM-635$_v$ (FERM P-9084) was cultured in a medium (30 ml in a 500 ml Sakaguchi flask), containing 2% of sucrose, 12% of amino acid mixture, 0.05% yeast extract, 0.1% of KH$_2$PO$_4$, and 0.5% of Na$_2$CO$_3$, under shaking at 30° C. for 3 days. The amount of alkaline cellulase produced was measured to obtain the results of 21,520 unit/liter.

EXAMPLE 4

The amount of alkaline cellulase production by Bacillus sp. KSM-635$_r$ (FERM P-9085) was measured following the manner as described in Example 3. The results obtained was 20,290 unit/liter.

REFERENCE EXAMPLE 3

Bacillus sp. KSM-2002 (FERM P-9450) was spread on the media E described below, each medium containing vancomycin or ristocetin at a concentration shown in Table 4 below, to determine minimum inhibitory concentration (MIC) of vancomycin or ristocetin. The medium E containing vancomycin or ristocetin to which Bacillus sp. KSM-2002 was spread and was left for 3 days at 30° C., and than the cell growth conditions on the medium surface was observed by naked eyes. The results are shown in Table 4.

Medium E:

| | |
|---|---|
| Bacto tryptone | 1.5% |
| Bacto soytone | 0.5% |
| NaCl | 0.5% |
| Bacto agar-agar | 2.0% |
| Vancomycin or Ristocetin | Concentration in Table 4 |
| | (pH 7.0) |

TABLE 4

| Concentration of vancomycin | Cell growth on medium surface | Concentration of ristocetin | Cell growth on medium surface |
|---|---|---|---|
| 0 (Control) | +++ | 0 (Control) | +++ |
| 0.008 γ | ++ | 0.008 γ | ++ |
| 0.01 γ | + | 0.01 γ | + |
| 0.02 γ | ± | 0.02 γ | + |
| 0.03 γ | − | 0.03 γ | ± |
| 0.04 γ | − | 0.04 γ | − |
| 0.05 γ | − | 0.05 γ | − |
| 0.1 γ | − | 0.1 γ | − |

As evident from the table, vancomycin and ristocetin MIC for Bacillus sp. KSM-2002 were about 0.02 γ and 0.03 γ, respectively.

EXAMPLE 5

Bacillus sp. KSM-2002 (FERM P-9450) was inoculated into the liquid medium F and cultured at 30° C. for 18 hours. NTG was added to the culture broth to the concentration of 30 to 100 γ, and the broth was left for 30–60 minutes at 20° C. Then, a 1% treated culture liquid was inoculated into the liquid medium and the culturing was continued at 30° C. overnight.

The culture liquid was spread on medium E containing not less than 0.02 γ of vancomycin or not less than 0.03 γ of ristocetin and cultured at 30° C. for 3 days. Colonies grown on the surface of the medium were collected. The above culturing procedure was repeated 5 times to obtain 7 vancomycin-resistant strains and 4 ristocetin-resistant strains.

Each of these strains was inoculated into 5 ml of liquid medium G in a test tube and cultured at 30° C. for 3 days. The alkaline protease titer was determined on each broth. As a result, high titer strains as shown in Table 5 were obtained. Among these, a vancomycin-resistant strain having the highest titer (No. 2016) and a ristocetin-resistant strain having the highest titer (No. 2014) were named Bacillus sp. KSM-2002ᵥ and Bacillus sp. KSM-2002ᵣ. The strains were deposited with Fermentation Research Institute, Agency of Industrial Science and Technology as FERM P-9939 and FERM P-9938, respectively.

| Medium F: | |
|---|---|
| Bacto tryptone | 1.5% |
| Bacto sottone | 0.5% |
| NaCl | 0.5% |
| | (pH 7.0) |

| Medium G: | |
|---|---|
| Glucose | 0.2% |
| Wool keratin | 0.5% |
| Yeast extract | 0.05% |
| $KH_2PO_4$ | 0.1% |
| $MgSO_4 \cdot 7H_2O$ | 0.02% |
| $Na_2CO_3$ | 0.4% |
| | (pH 9.0) |

TABLE 5

| Mutant No. | Vancomycin Resistance | Alkaline protease Production | Mutant No. | Ristocetin Resistance | Alkaline protease Production |
|---|---|---|---|---|---|
| 2003 | 0.05 γ | 2.23 A.U./l | 2012 | 0.05 γ | 1.45 A.U./l |
| 2016 | 0.05 γ | 2.78 A.U./l | 2013 | 0.05 γ | 1.86 A.U./l |
| 2006 | 0.06 γ | 1.43 A.U./l | 2014 | 0.05 γ | 2.53 A.U./l |
| Bacillus sp. KSM-2002 (Parent strain: Control) | 0.02 γ | 0.71 A.U./l | Bacillus sp. KSM-2002 (Parent strain: Control) | 0.03 γ | 0.71 A.U./l |

REFERENCE EXAMPLE 5

Bacillus amyloliquefaciens KSM-22 (ATCC 23845) was spread on the medium E, each medium containing vancomycin or ristocetin at a prescribed concentration, to determine minimum inhibitory concentration (MIC) of vancomycin or ristocetin in the same manner as in Reference Example 3. The results are shown in Table 6.

TABLE 6

| Concentration of vancomycin | Cell growth on medium surface | Concentration of ristocetin | Cell growth on medium surface |
|---|---|---|---|
| 0 (Control) | +++ | 0 (Control) | +++ |
| 0.09 γ | ++ | 0.7 γ | ++ |
| 0.1 γ | ++ | 0.8 γ | + |
| 0.2 γ | + | 0.9 γ | ± |
| 0.3 γ | ± | 1.0 γ | − |
| 0.4 γ | − | 1.3 γ | − |
| 0.5 γ | − | 1.5 γ | − |
| 1.0 γ | − | | |

EXAMPLE 6

Bacillus amyloliquefaciens KSM-22 (ATCC 23845) was inoculated into the liquid medium F and cultured at 30° C. for 16 hours. NTG was added to the culture broth to a concentration of 30 to 100 γ and the broth was left for 30–60 minutes at 20° C. Then, a 1% treated culture liquid was inoculated into the liquid medium and the culturing was continued at 30° C. overnight.

The culture liquid was spread on medium E containing not less than 0.3 γ of vancomycin or 0.9 γ of ristocetin and cultured at 30° C. for 3 days. Colonies grown on the surface of the medium were collected. The above culturing procedure was repeated 5 times to obtain 5 vancomycin-resistant strains and 4 ristocetin-resistant strains.

Each of these strains was inoculated into 5 ml of liquid medium F and cultured at 30° C. for 2 days. The amylase titer was determined on each broth. As a result, high titer strains as shown in Table 7 were obtained. Among these, a vancomycin-resistant strain having the highest titer (No. 4591) and a ristocetin-resistant strain having the highest titer (No. 4551) were named Bacillus

*amyloliquefaciens* KSM-22ᵥ and *Bacillus amyloliquefaciens* KSM-22ᵣ. The strains were deposited with Fermentation Research Institute, Agency of Industrial Science and Technology as FERM P-9937 and FERM P-9936, respectively.

TABLE 7

| Mutant No. | Vancomycin Resistance | Amylase Production | Mutant No. | Ristocetin Resistance | Amylase Production |
|---|---|---|---|---|---|
| 4504 | 0.5 γ | 20900 unit/l | 4551 | 2.0 γ | 49400 unit/l |
| 4591 | 0.5 γ | 46900 unit/l | 4554 | 2.0 γ | 13050 unit/l |
| *Bacillus amyloliquefaciens* KSM-22 (ATCC 23845) (Parent strain: Control) | 0.3 γ | 10700 unit/l | *Bacillus amyloliquefaciens* KSM-22 (ATCC 23845) (Parent strain: Control) | 0.9 γ | 10700 unit/l |

Obviously, numerous modifications and variations of the present invention are possible in light of the above teachings. It is therefore to be understood that the scope of the appended claims, the invention may be practiced otherwise than as specifically described herein.

Strains have been deposited with
(a) The Fermentation Research Institute, Agency of Industrial Science and Technology, Ministry of International Trade and Industry, 1-3, Higashi, 1-Chome, Yatabe-Machi, Tsukuba-Gun, Ibraki-Ken 305, Japan and
(b) The American Type Culture Collection, 12301 Parklawn Drive, Rockville, Md. 20852, USA.

What is claimed as new and desired to be secured by Letters Patent:

1. A biologically pure cellulase, protease or amylase-producing microorganism belonging to the genus Bacillus selected from the group consisting of Bacillus sp. KSM-635 (FERM P-9084), Bacillus sp. KSM-635, (FERM P-9085), Bacillus sp. KSM-2002, (FERM P-9939), Bacillus sp. KSM-2002, (FERM P-9938), *Bacillus amyloliquefaciens* KSM-22 (FERM P-9937) and *Bacillus amyloliquefaciens* KSM-22, (FERM P-9936).

2. A process for producing a cell membrane synthesis inhibitor-resistant mutant of a cellulase, protease or amylase-producing microorganism belonging to genus Bacillus, comprising:
  subjecting a cellulase, protease or amylase-producing microorganism of the genus Bacillus to a mutation treatment, and
  culturing said microorganism in a culture medium containing a cell membrane synthesis inhibitor selected from the group consisting of vancomycin and ristocetin.

3. The process of claim 2 wherein the mutation treatment is performed on a microorganism selected from the group consisting of Bacillus sp. KSM-635 (FERM P-8872), Bacillus sp. KSM-425, Bacillus sp. KSM-521, Bacillus sp. KSM-580, Bacillus sp. KSM-2002 (FERM P-9450), Bacillus sp. KSM-2001, Bacillus sp. KSM-2003, Bacillus sp. KSM-2005, *Bacillus amyloliquefaciens* KSM-22 (ATCC 23845), *Bacillus amyloliquefaciens* KSM-21 (ATCC 23844) and *Bacillus licheniformis* KSM-23 (ATCC 27811).

* * * * *